US009937053B2

(12) United States Patent
Melkent et al.

(10) Patent No.: US 9,937,053 B2
(45) Date of Patent: Apr. 10, 2018

(54) EXPANDABLE INTERBODY IMPLANT (71) Applicant: Warsaw Orthopedic, Inc., Warsaw, IN (US)

(72) Inventors: Anthony J. Melkent, Germantown, TN (US); William D. Armstrong, Memphis, TN (US); Stanley T. Palmatier, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 657 days.

(21) Appl. No.: 14/532,636

(22) Filed: Nov. 4, 2014

(65) Prior Publication Data
US 2016/0120660 A1 May 5, 2016

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/30428* (2013.01); *A61F 2002/30471* (2013.01); *A61F 2002/30507* (2013.01); *A61F 2002/30538* (2013.01); *A61F 2002/30904* (2013.01); *A61F 2002/4475* (2013.01)

(58) Field of Classification Search
CPC ............ A61F 2/4455–2/447; A61F 2002/4475
See application file for complete search history.

(56) References Cited

U.S. PATENT DOCUMENTS

| 6,491,724 | B1 | 12/2002 | Ferree |
| 7,828,849 | B2 | 11/2010 | Lim |
| 7,850,733 | B2 | 12/2010 | Baynham et al. |
| 7,875,078 | B2 | 1/2011 | Wysocki et al. |
| 7,909,869 | B2 | 3/2011 | Gordon et al. |
| 8,062,375 | B2 | 11/2011 | Glerum et al. |
| 8,105,358 | B2 | 1/2012 | Phan |
| 8,105,382 | B2 | 1/2012 | Olmos et al. |
| 8,123,810 | B2 | 2/2012 | Gordon et al. |
| 8,133,232 | B2 | 3/2012 | Levy et al. |
| 8,187,332 | B2 | 5/2012 | McLuen |
| 8,382,842 | B2 | 2/2013 | Greenhalgh et al. |
| 8,394,145 | B2 | 3/2013 | Weiman |
| 8,398,713 | B2 | 3/2013 | Weiman |
| 8,403,990 | B2 | 3/2013 | Dryer et al. |

(Continued)

*Primary Examiner* — Matthew Lawson
*Assistant Examiner* — Amy Sipp (57) ABSTRACT

An expandable interbody implant adapted for insertion at least into a disc space, between two adjacent vertebrae of a spine. An upper member and a lower member are pivotally connected at least by a drive link. A bone graft storage portion packed with a selected volume of bone growth material. A translational wall is provided between the bone graft storage portion and a trailing end of the implant. An actuator engages the bone graft storage portion, pushing it forward into engagement with the drive link, which pivots upward, moving the upper member upward away from the lower member. Upward movement of the upper member raises the translational wall to a position to assist in retention of the selected volume bone graft material within the hollow portion of the bone graft storage portion. Upward rotation of the drive link brings a face thereof into contact with a front of the bone graft storage portion, thereby retaining near constant volume of the bone graft material.

20 Claims, 7 Drawing Sheets

(56) References Cited

U.S. PATENT DOCUMENTS

| | | |
|---|---|---|
| 8,435,298 B2 | 5/2013 | Weiman |
| 8,491,659 B2 | 7/2013 | Weiman |
| 8,518,120 B2 | 8/2013 | Glerum et al. |
| 8,523,944 B2 | 9/2013 | Jimenez et al. |
| 8,556,979 B2 | 10/2013 | Weiman et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum |
| 8,940,049 B1 * | 1/2015 | Jimenez .................. A61F 2/447 623/17.15 |
| 9,039,771 B2 | 5/2015 | Glerum et al. |
| 9,119,730 B2 | 9/2015 | Glerum et al. |
| 9,801,734 B1 * | 10/2017 | Stein ....................... A61F 2/447 |
| 2002/0068977 A1 | 6/2002 | Jackson |
| 2006/0206207 A1 | 9/2006 | Dryer et al. |
| 2011/0054621 A1 | 3/2011 | Lim |
| 2011/0172721 A1 | 7/2011 | Varela et al. |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1 * | 6/2013 | Palmatier ................ A61F 2/447 623/17.16 |
| 2013/0190876 A1 | 7/2013 | Drochner et al. |
| 2014/0121774 A1 | 5/2014 | Glerum et al. |
| 2014/0324171 A1 | 10/2014 | Glerum et al. |
| 2016/0250034 A1 * | 9/2016 | Loebl ....................... A61F 2/44 623/17.16 |

\* cited by examiner

EXPANDABLE INTERBODY IMPLANT

BACKGROUND OF THE INVENTION

The present invention relates generally to an expandable interbody implant, and more particularly to a lordotic expandable interbody implant adapted for oblique posterior, oblique anterior, co-axial posterior, or co-axial anterior, insertion and placement in a disc space having a surgically-corrected height between adjacent vertebral bodies in the lumbar spine.

DESCRIPTION OF THE RELATED ART

Lordotic expandable spinal fusion implants are known in the art. The lordotic, tapered configuration of such known implants assists in the restoration or enhancement of spinal lordosis in the lumbar spine. The expandability of such implants allows placement of a potentially larger implant through a smaller opening in a patient's body, with selective expansion in a selected direction providing the advantage of increasing the height of the implant and corresponding distraction of the disc space, without a concomitant increase in the width of the implant. The related art implants, however, have certain disadvantages.

For example, the configurations of the leading ends of the related art implants limit the preferred placement of the implants in the disc space to be along an axis defined between the anterior and posterior portion of the disc space. Oblique placement has not been optimized with the related art implants.

The related art implants, moreover, typically employ ramp-on-ramp linkage mechanisms, which have proven to be unreliable in enabling such implants to smoothly and reliably increase to a selected height desired by the surgeon.

In addition, the related art implants have experienced difficulty with maintaining, during insertion and expansion within the disc space, a selected volume of bone graft material stored in the implant. During expansion of such related-art implants within the disc space, some of the stored bone graft material often escapes, thereby reducing the selected volume of bone graft material stored in the implant.

SUMMARY OF THE INVENTION

It is an object of the present invention to provide an expandable interbody implant adaptable to allow placement of a potentially larger implant through a smaller opening in a patient's body, including, but not limited to, placement into a surgically-corrected disc space between two adjacent vertebrae of a spine.

It is another object of the present invention to provide an expandable interbody implant which can, in one embodiment, be inserted at an oblique angle with respect to an axis defined between an anterior surface and a posterior surface of a disc space, and in other embodiments, also be inserted along the axis from the anterior surface or the posterior surface.

It is a further object of the present invention to provide an expandable interbody implant having an improved driving link, enabling a surgeon to smoothly and reliably expand the implant to a selected height.

It is a further object of the present invention to provide an expandable interbody implant that maintains a near-constant graft volume chamber to avoid formation of pockets in the bone graft as the implant expands.

It is a further object of the present invention to provide an expandable interbody implant with improved control over loss, during expansion, of bone graft material stored within the implant.

These and other objects of the present invention will be apparent from review of the following specification and the accompanying drawings.

In view of the above objects, an expandable interbody implant, in accordance with the present invention, includes a leading end, and a trailing end, adapted for insertion at least into a disc space having a surgically-corrected height, between two adjacent vertebrae of a spine.

An upper member has an upper surface extending between the leading end and the trailing end, and an upper opening defined in the upper surface.

A lower member has a lower surface extending between the leading end and the trailing end, pivotally connected to the upper member at least via a drive link, and a lower opening defined in the lower surface.

A bone graft storage portion is provided intermediate the leading end and the trailing end, including a hollow portion configured to be packed with a selected volume of bone growth material and adapted to allow bone growth between the adjacent vertebrae via the upper and lower openings and the bone graft storage portion. A translational wall is movably mounted between the bone graft storage portion and the trailing end.

An actuator opening is defined proximate the trailing end, and configured for insertion therein of an actuator.

The actuator, following insertion thereof into the actuator opening, pushes the bone graft storage portion toward the leading end and into engagement with the drive link, thereby pushing the drive link forward and moving the upper member upward away from the lower member.

The drive link includes an elongated member having opposing first and second ends, the first end being pivotally attached to the upper member proximate the leading end, and the second end being movably mounted on the lower member proximate the bone graft storage portion, and a ramp portion having a surface defined between the first end and the second end.

The bone graft storage portion, when being pushed forward by the actuator, is adapted to engage the second end of the drive link, pushing it along the lower member, thereby resulting in pivotable translation between the first end of the drive link and the upper member.

The pivotable translation between the first end of the drive member and the upper member continues until the surface of the ramp portion engages the front end of the bone graft storage portion.

The translational wall is mounted in a track at a rear portion of the hollow portion. Pivoting the upper member upward engages the translational wall, thereby raising it upward in the track. An upper surface of the translational wall is adapted to remain substantially flush with an inner surface of the upper member, thereby assisting in preventing loss of the bone graft material from the hollow portion of the bone graft storage portion.

The surface of the ramp of the drive link comes into contact with a front end of the bone graft storage portion, thereby preventing formation of pockets in the bone graft material and keeping the volume of the bone graft material substantially constant.

DETAILED DESCRIPTION OF THE PREFERRED EMBODIMENTS

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims.

As shown in FIGS. 1-7, an expandable interbody implant 20 includes a leading end 22 and a trailing end 24. Implant 20 is adapted for insertion at least into a disc space having a surgically-corrected height between two adjacent vertebrae of a spine. Implant 20, moreover, is adapted for movement from an unexpanded position to an expanded position.

Implant 20 includes an upper member 26, having an upper surface 28 extending between leading end 22 and trailing end 24, with an upper opening 30 defined in upper surface 28.

Implant 20 further includes a lower member 32, having a lower surface 34 extending between leading end 22 and trailing end 24, with a lower opening 36 defined in lower surface 34.

Figure 2:
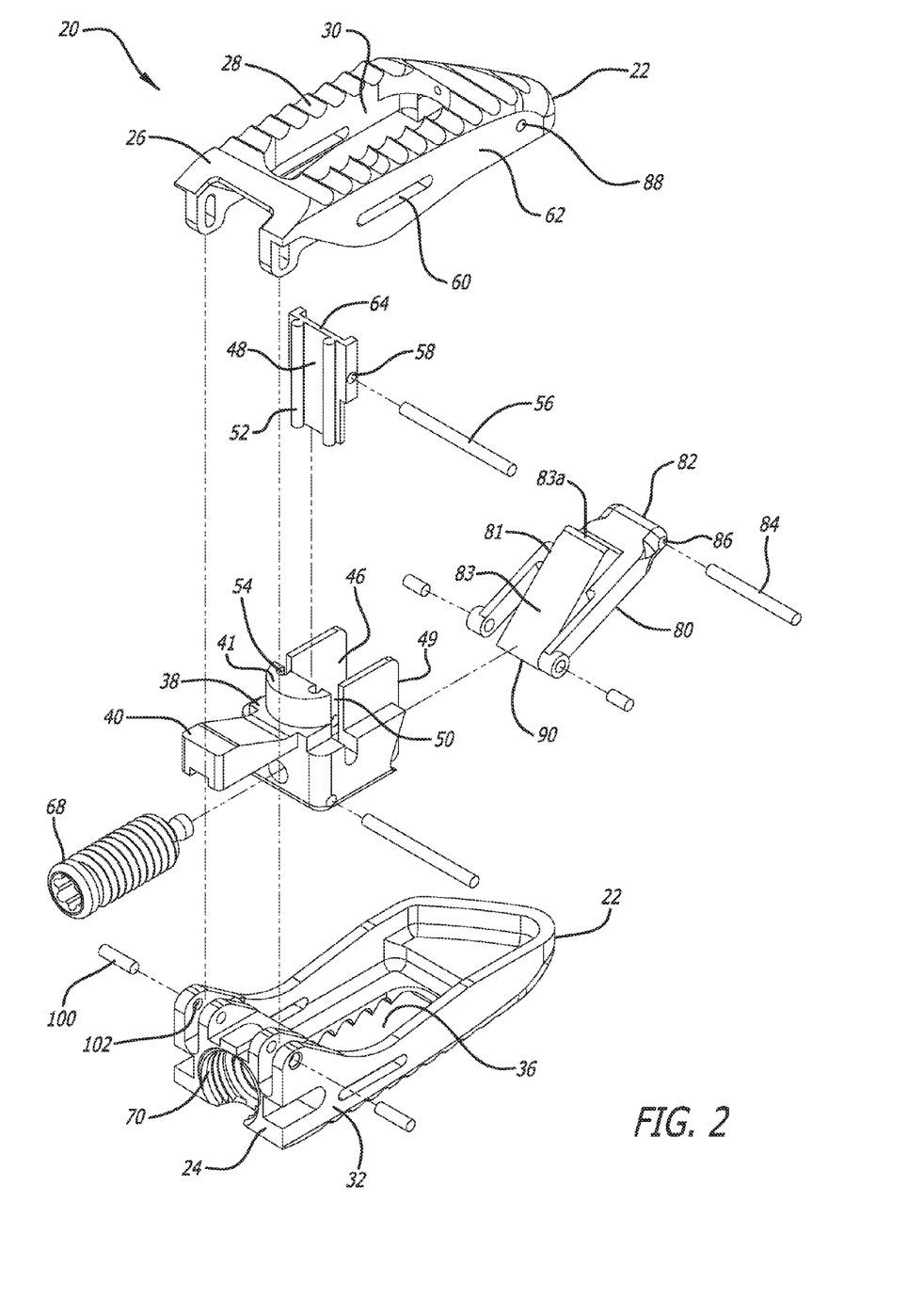
FIG. 2 is an exploded perspective view of an expandable interbody implant in accordance with the present invention.
Figure 5:
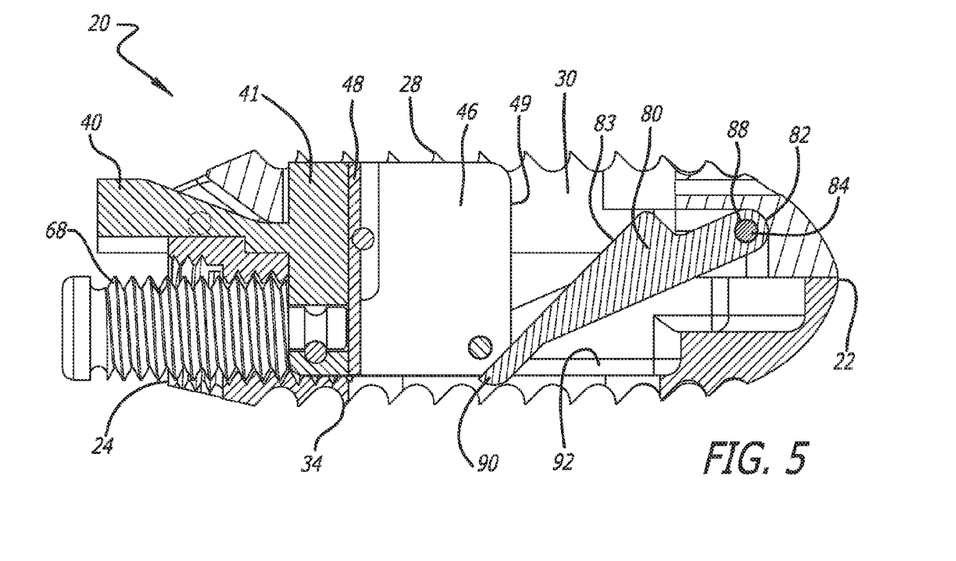
FIG. 5 is a cross-sectional side view of an expandable interbody implant in accordance with the present invention, in an unexpanded position.
Figure 6:
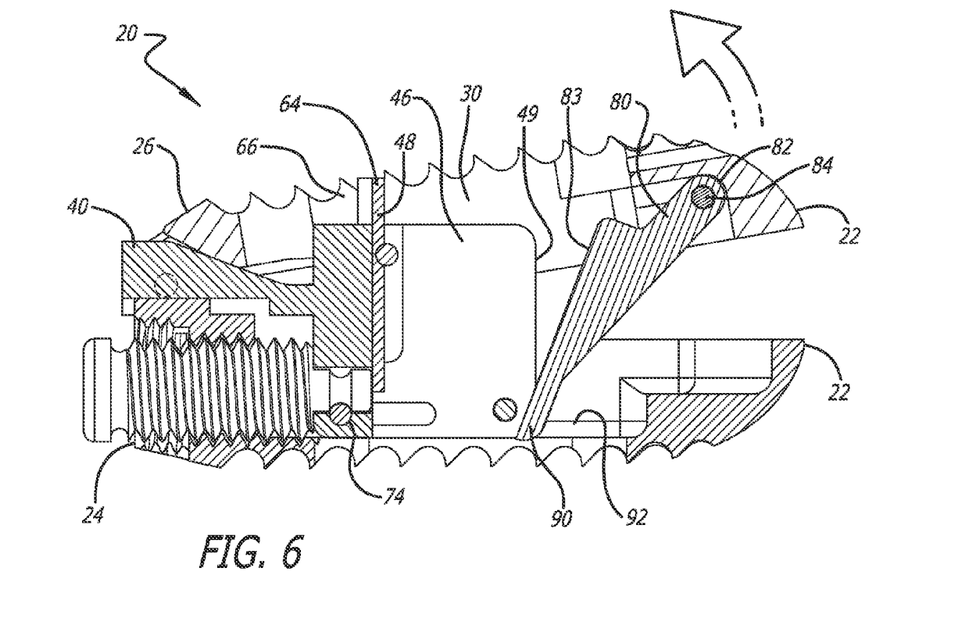
FIG. 6 is a cross-sectional side view of an expandable interbody implant in accordance with the present invention, in a partially-expanded position.

A bone graft storage portion 38 is preferably provided intermediate leading end 22 and trailing end 24. As shown in FIGS. 2 and 5-6, the bone graft storage portion 38 includes a rearward-extending portion 40, a rear end portion 41, and a hollow portion 46 sized to receive a selected volume of bone graft material, which may be of a type well-known in the art. As shown in FIG. 2, the side walls of hollow portion 46 align with rear portions of the sides of the upper and lower openings 30 and 36. Once implant 20 is implanted in the disc space, the bone graft material is adapted to facilitate bone growth between the adjacent vertebrae, via upper opening 30, hollow portion 46, and lower opening 36. In a preferred embodiment, as shown in FIGS. 2-6, end portion 41 has a generally hemi-cylindrical configuration generally corresponding in shape to a portion of the perimeter of upper opening 30.

In a preferred embodiment, and as shown in FIGS. 2-6, a translational wall 48 is movably provided in a slot 50 provided in bucket portion 38 between rear end portion 41 and hollow portion 46. Preferably, translational wall 48 includes a pair of vertical extensions 52, slidably mounted in a pair of tracks 54 defined in end portion 41. As shown in FIG. 2, vertical extensions 52 and tracks 54 have a cylindrical configuration, but any configuration, e.g., a rectangular configuration, is within the scope of the invention. In addition, a pin 56 extends through an aperture 58 in the translational wall 48. As shown in FIGS. 1-3, and 7, pin 56 inserts through an oval-shaped aperture 60 defined in a side wall 62 of upper member 26. Pin 56 is adapted to slide in the oval-shaped aperture 60.

An actuator 68 is adapted to be inserted into and move through an actuator opening 70 in trailing end 24 of implant 20. Preferably, actuator 68 is a threaded actuator having a threaded portion 72 and an actuating end 74. The threads defined on threaded portion 72 are configured to threadably engage corresponding threads in actuator opening 70. A threaded actuator and threaded opening are preferred because, once implant 20 is expanded, the threaded engagement between actuator 68 and actuator opening 70 assists in retaining implant 20 in its expanded position. The invention, however, is not limited to use with a threaded actuator or threaded actuator opening. Other actuator configurations, and corresponding actuator opening configurations, which are well-known in the art can be used, and are within the scope of the invention.

The implant includes a drive link 80. Drive link 80 preferably is configured as an elongated member having a first end 82, and an opposed second end 90, and a ramp portion 81 intermediate the two opposing end portions, ramp portion 81 including a face portion 83 terminating in a peak portion 83a. As shown in FIGS. 2 and 5-6, first end 82 includes an elongated pin 84 extending through an aperture 86 in the first end, and also through an aperture 88 defined in side wall 62 of upper member 26, proximate leading end 22. As further shown in FIGS. 2 and 5-6, second end 90 is movably mounted on an inner surface 92 of lower member 32.

Figure 7:
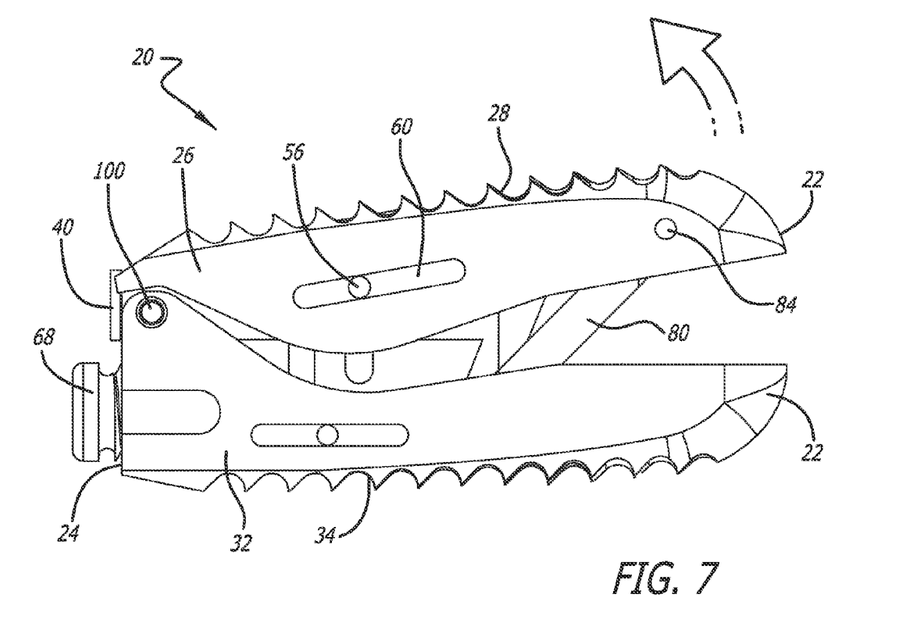
FIG. 7 is a side view of an expandable interbody implant in accordance with the present invention, in the partially-expanded position.

Insertion and placement of a preferred embodiment of the expandable interbody implant in accordance with the present invention will be explained below:

As shown in FIGS. 5-7, forward movement of actuator 68 brings actuating end 74 into contact with rear end portion 41 of bucket portion 38. Bucket portion 38, including hollow portion 46 is pushed forward until the front of hollow portion 46 engages second end 90 of drive link 80. Second end 90 of drive link 80 is pushed forward on inner surface 92 of lower member 32, causing first end 82 and ramp portion 81 of drive link 80 to pivot upward. The upward movement of first end 82 pushes upper member 26 upward, in an upward pivotal motion, up and away from lower member 32, pivoting on a pair of pins 100, inserted through apertures 102, which join upper and lower members 26 and 32 together proximate trailing end 24.

As upper member 26 moves upward, pin 56 slides in oval-shaped aperture 60, thereby raising translational wall 48 upward, as shown in FIG. 6. As shown in FIGS. 5-6, as a result of this configuration, an upper surface 64 of translational wall 48, which is substantially flush with an inner surface 66 of upper member 26 when implant 20 is in the unexpended position, continues to remain substantially flush with inner surface 66 of upper member 26, throughout the upward pivotal movement of upper member 26. As further shown in FIG. 6, the upward movement of upper wall 48 corresponding to the pivotal upward movement of upper member 26 raises translational wall 48 to a position where it substantially prevents any of the selected volume of bone graft material packed into a bone graft storage portion 46 from escaping out of the bone graft storage space in the direction of translational wall 48 during expansion of the implant, thereby helping to retain the selected volume of bone graft material within implant 20.

Pivotal upward expansion of upper member 26 is limited by face portion 83 of the ramp portion 81 of drive link 80. Face 83 eventually comes into contact with a front surface 49 of the bucket portion 38, thereby acting as a stop, and preventing further pivotal expansion of the implant 20.

Moreover, as the bone graft storage portion 38 moves forward to actuate the implant, the graft volume defined by the bone graft storage portion on the face portion 83 on the "front end," and the upper and lower endplates of the adjacent vertebral bodies (via the upper and lower openings 30 and 36 respectively), remains substantially constant because, as the top-to-bottom dimension of the implant increases with expansion, the front-to-back dimension of the hollow portion 46 between the translational wall 48 and the face 83 in contact with the front surface 49 decreases simultaneously, thereby reducing formation of pockets in the bone graft material stored in the bone graft storage portion 38.

Leading end 22 of implant 20 can have different configurations.

Figure 1:
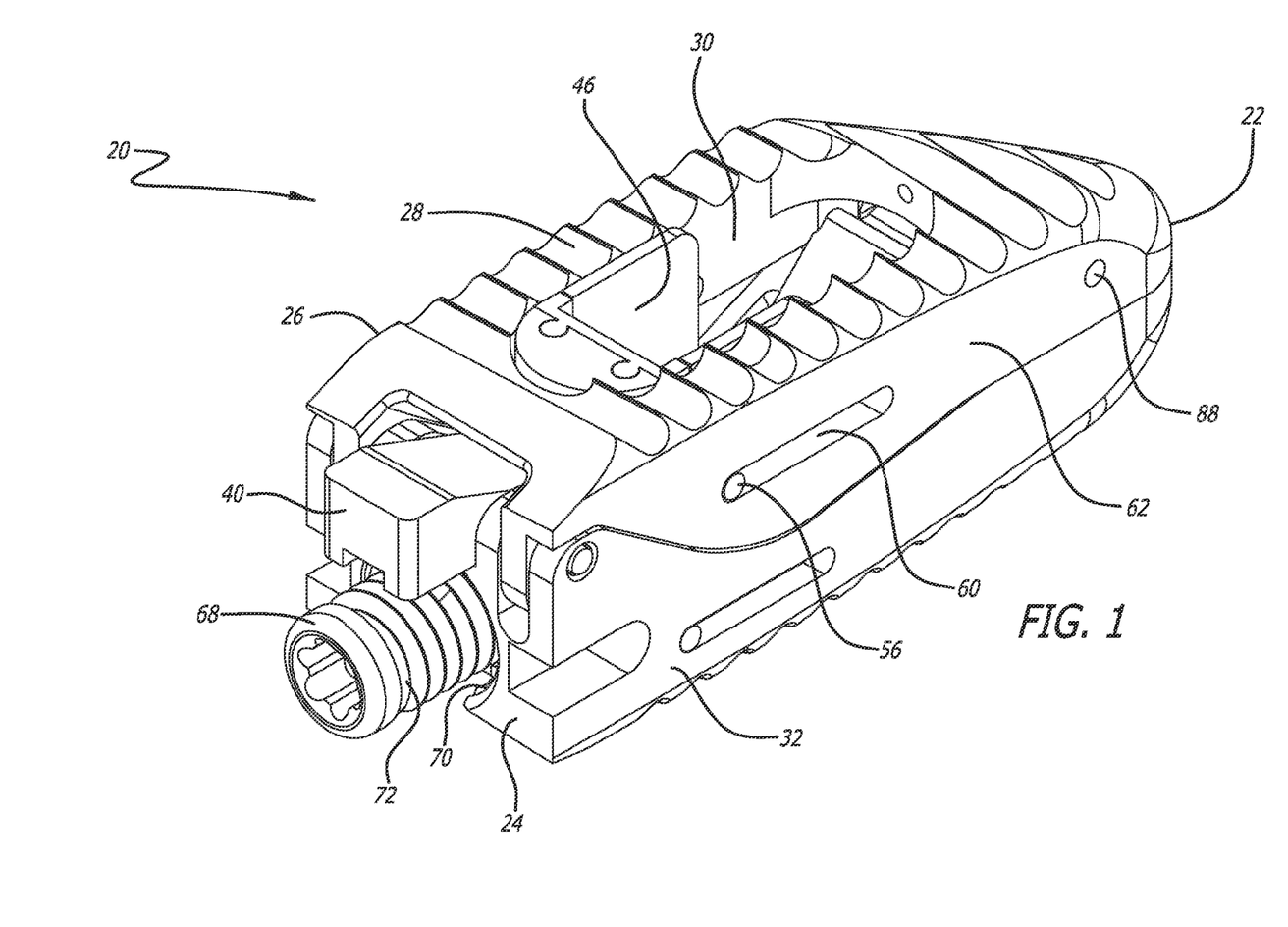
FIG. 1 is a trailing end perspective view of an expandable interbody implant accordance with an embodiment of the present invention.

In one preferred embodiment, as shown in FIGS. 1-2, leading end 22 has a substantially rounded, bullet-shaped configuration.

Figure 3:
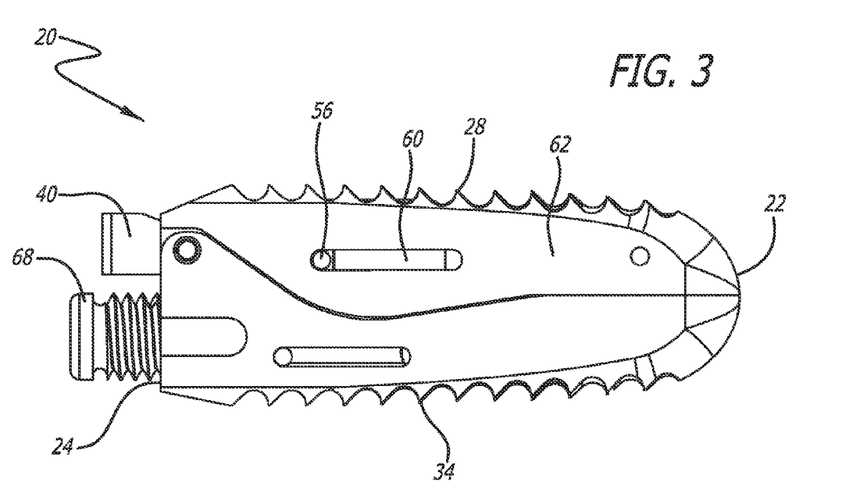
FIG. 3 is a side elevational view of one embodiment of an expandable interbody implant in accordance with the present invention, adapted for oblique, anterior, or posterior insertion and placement in a disc space.
Figure 4:
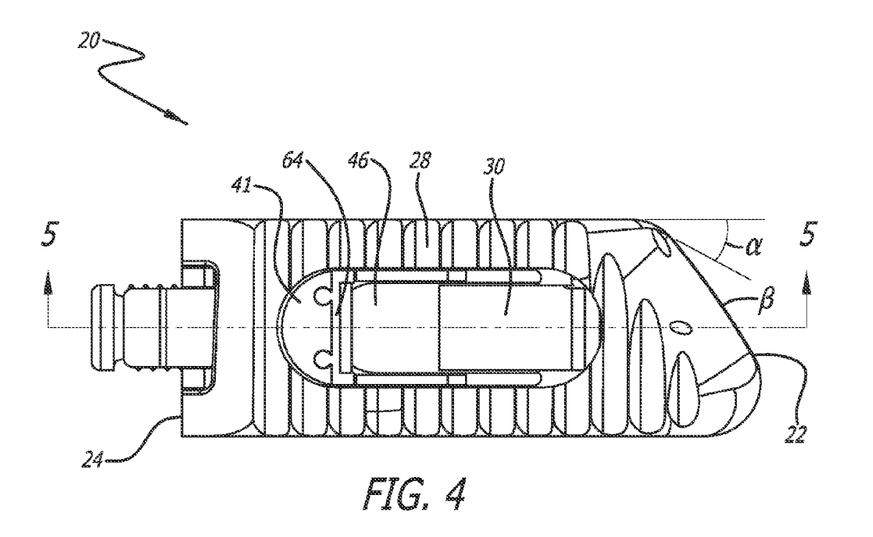
FIG. 4 is a top view of the embodiment of FIG. 3.
Figure 9:
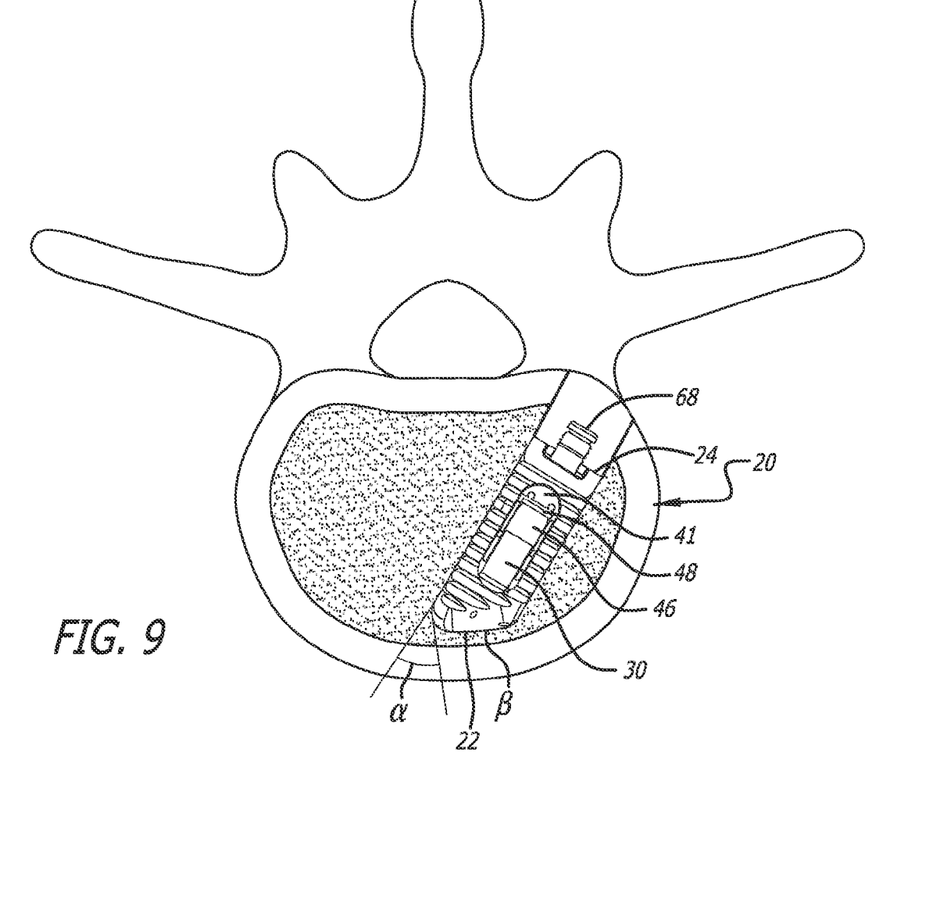
FIG. 9 is a top view of an expandable interbody implant in accordance with the present invention, having a beveled leading end, inserted into a surgically-corrected disc space between two adjacent vertebrae of a spine, at an oblique angle with respect to an axis extending from an anterior portion of the disc space to a posterior portion of the disc space.

In another preferred embodiment, as shown in FIGS. 3-4, and 9, leading end 22 has a beveled surface β defining an oblique angle α between upper surface 28 and lower surface 34. Oblique angle α preferably is approximately 45°. As shown in FIG. 9, beveled leading end 22 of this embodiment is capable of insertion into the disc space at an oblique angle, preferably 45°, with respect to the axis defined between anterior and posterior portions of the disc space. The beveled leading end of this embodiment also is capable of insertion into the disc space along the axis defined between anterior and posterior portions of the disc.

Figure 8:
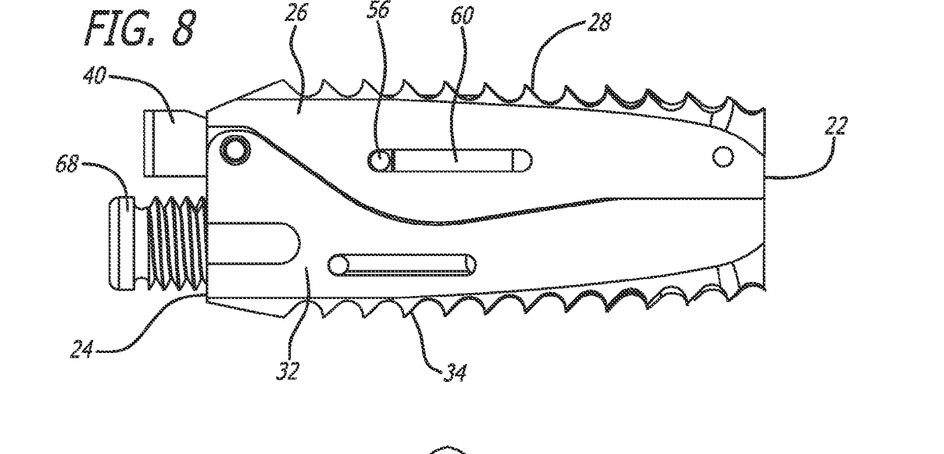
FIG. 8 is a side elevational view of another embodiment of an expandable interbody implant in accordance with the present invention.
Figure 10:
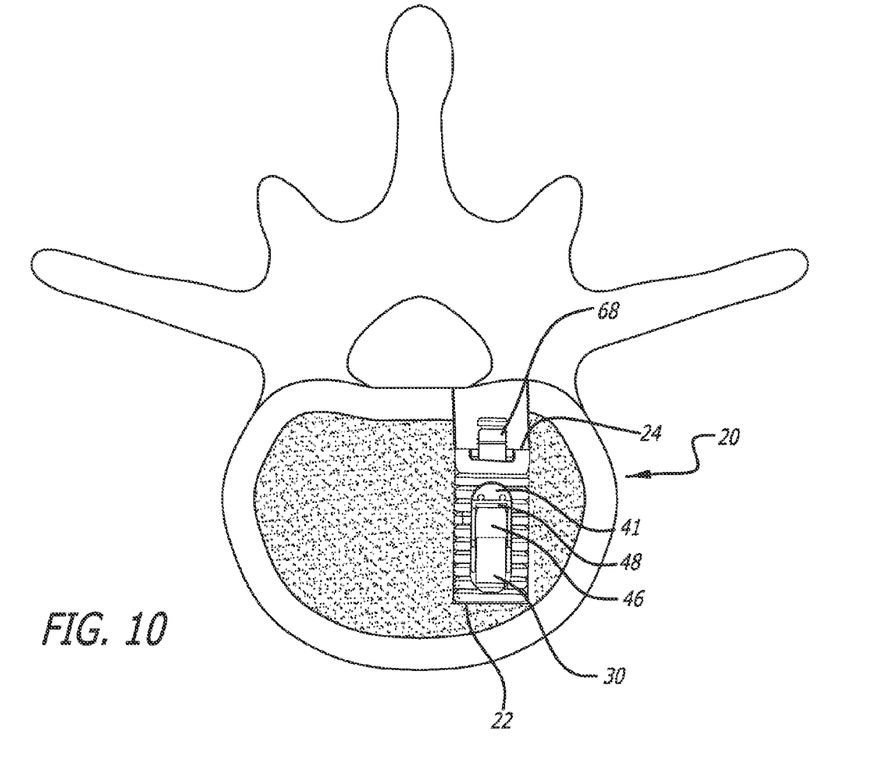
FIG. 10 is a top view of an expandable interbody implant in accordance with the invention, having a substantially vertical planar leading end, inserted into a surgically-corrected disc space between two adjacent vertebrae of a spine, along an axis extending from a posterior portion of the disc space to an anterior portion of the disc space.

In another embodiment, as shown in FIG. 8, leading end 22 has a generally planar shape, defining substantial right angles with respect to each of upper and lower surfaces 28 and 34, respectively. As shown in FIG. 10, leading end 22 of this embodiment also is configured for insertion of the implant into the disc space at least along the axis defined between anterior and posterior portions of the disc space.

There is disclosed in the above description and the drawings, implants, which fully and effectively accomplish the objectives of this invention. It will be apparent, however, that variations and modifications of the disclosed embodiments may be made without departing from the principles of the invention or the scope of the appended claims.

What is claimed is:

1. An expandable interbody implant comprising:
   a leading end and an opposite trailing end, the expandable interbody implant being adapted for insertion at least into a disc space between two adjacent vertebrae;
   an upper member having an upper surface extending between the leading end and the trailing end, and an upper opening defined in the upper surface;
   a lower member having a lower surface extending between the leading end and the trailing end, and a lower opening defined in the lower surface, the lower member being pivotally connected to the upper member at least via a drive link;
   a bone graft storage portion provided intermediate the leading end and the trailing end, the bone graft storage portion including a hollow portion configured to be packed with a selected volume of bone growth material and adapted to allow bone growth between the adjacent vertebrae via the upper and lower openings and the bone graft storage portion, and the bone graft storage portion being non-rotatable and capable of movement between a first position and a second position, the first position being closer to the trailing end than the second position;
   a translational wall movably mounted between the bone graft storage portion and the trailing end; and
   an actuator opening and an actuator, the actuator opening being positioned proximate the trailing end and being configured for insertion of the actuator therein, the actuator being engaged to the bone graft storage portion and being configured to move the bone graft storage portion between the first position and the second position,
   wherein movement of the bone graft storage portion from the first position toward the second position moves the bone graft storage portion into engagement with the drive link, thereby moving the drive link forward and pivoting the upper member upward away from the lower member; and
   wherein pivoting the upper member upward engages the translational wall, thereby moving the translational wall to a position adapted to assist in preventing loss of the bone graft material from the bone graft storage portion.

2. The expandable interbody implant of claim 1, wherein the drive link comprises an elongated member having opposing first and second ends, the first end pivotally attached to the upper member proximate the leading end, and the second end movably mounted on the lower member proximate the bone graft storage portion.

3. The expandable interbody implant of claim 2, wherein the bone graft storage portion, when being moved from the first position toward the second position by the actuator, is adapted to engage the second end of the drive link, moving it along the lower member, thereby resulting in pivotable translation between the first end of the drive link and the upper member.

4. The expandable interbody implant of claim 3, wherein the drive link further comprises a ramp portion intermediate the first and second ends, the ramp portion having a surface, wherein the pivotal translation between the first end of the drive member and the upper member continues until the surface of the ramp portion engages a front end of the bone graft storage portion.

5. The expandable interbody implant of claim 1, wherein the upper member and the lower member are further pivotally connected proximate the trailing end.

6. The expandable interbody implant of claim 1, wherein the translational wall is mounted in a track at a rear portion of the hollow portion, and pivoting the upper member upward raises the translational wall in the track.

7. The expandable interbody implant of claim 6, wherein an upper surface of the translational wall is adapted to remain substantially flush with an inner surface of the upper member.

8. The expandable interbody implant of claim 1, wherein the leading end defines a substantially vertical, substantially planar surface.

9. The expandable interbody implant of claim 1, wherein the leading end defines a beveled surface.

10. The expandable interbody implant of claim 1, wherein the leading end defines a substantially rounded surface.

11. The expandable interbody implant of claim 1, wherein the bone graft storage portion is adapted to interact with at least one of the drive link and the translational wall to maintain a substantially constant volume of the bone graft material therein during the implant expansion.

12. An expandable interbody implant comprising:
a leading end and an opposite trailing end, the expandable interbody implant being adapted for insertion at least into a disc space between two adjacent vertebrae;
an upper member having an upper surface extending between the leading end and the trailing end, and an upper opening defined in the upper surface;
a lower member having a lower surface extending between the leading end and the trailing end, and a lower opening defined in the lower surface;
a bone graft storage portion provided intermediate the leading end and the trailing end, the bone graft storage portion including a hollow portion configured to be packed with a selected volume of bone growth material and adapted to allow bone growth between the adjacent vertebrae via the upper and lower openings and the bone graft storage portion, and the bone graft storage portion being non-rotatable and capable of movement between a first position and a second position, the first position being closer to the trailing end than the second position;
a translational wall movably mounted between the bone graft storage portion and the trailing end;
an elongated drive link pivotally connecting the upper member and the lower member, the elongated drive link having first and second ends, the first end being pivotally attached to the upper member proximate the leading end, and the second end being movably mounted on the lower member proximate the bone graft storage portion; and
an actuator opening and an actuator, the actuator opening being positioned proximate the trailing end and being configured for insertion of the actuator therein, the actuator being engaged to the bone graft storage portion and being configured to move the bone graft storage portion between the first position and the second position;
wherein movement of the bone graft storage portion from the first position toward the second position moves the bone growth storage portion into engagement with the drive link, thereby pivoting the upper member upward to a height substantially equal to a height between the adjacent vertebrae.

13. The expandable interbody implant of claim 12, wherein the pivotable upward movement of the upper member engages the translational wall, thereby moving the translational wall upward.

14. The expandable interbody implant of claim 12, wherein the translational wall comprises at least one pin inserted therethrough in a direction generally transverse to a longitudinal axis of the implant, at least one end of the pin adapted to extend through a generally oval-shaped aperture defined in at least one sidewall of the upper member.

15. The expandable interbody implant of claim 14, wherein a length of the generally oval-shaped aperture is adapted such that, as the upper member pivots upward a selected distance, the at least one pin moves in the generally oval-shaped aperture a corresponding amount to move the translational wall upward and retain an upper end of the translational wall substantially flush with an inner surface of the upper member.

16. The expandable interbody implant of claim 12, wherein the leading end defines a substantially vertical substantially planar surface.

17. The expandable interbody implant of claim 12, wherein the leading end defines a beveled surface.

18. The expandable interbody implant of claim 12, wherein the leading end defines a substantially rounded surface.

19. The expandable interbody implant of claim 12, wherein the bone graft storage portion is adapted to interact with at least one of the drive link and the translational wall to substantially maintain the selected volume of bone growth material in the hollow portion during the implant expansion.

20. An expandable interbody implant comprising:
a leading end and an opposite trailing end the expandable interbody implant being adapted for insertion at least into a disc space between two adjacent vertebrae;
an upper member having an upper surface extending between the leading end and the trailing end, and an upper opening defined in the upper surface;
a lower member having a lower surface extending between the leading end and the trailing end, and a lower opening defined in the lower surface;
a bone graft storage portion intermediate the leading end and the trailing end, the bone graft storage portion being configured to be packed with a selected volume of bone growth material and adapted to allow bone growth between the adjacent vertebrae via the upper and lower openings, and the bone graft storage portion being non-rotatable and capable of movement between a first position and a second position, the first position being closer to the trailing end than the second position;
a translational wall movably mounted between the bone graft storage portion and the trailing end; and
an elongated drive link pivotally connecting the upper member and the lower member, the elongated drive link having first and second ends, the first end being pivotatally attached to the upper member proximate the leading end, and the second end being movably mounted on the lower member proximate the bone graft storage portion;
wherein the bone graft storage portion is positioned and adapted, upon actuation of the implant and movement of the bone graft storage portion from the first position toward the second position, to drive the second end of the drive link toward the leading end, thereby moving the first end of the drive link upward;
wherein the first end of the drive link is adapted to raise the upper member pivotally upward; and
wherein the upward movement of the upper member is adapted to raise the translational wall.

* * * * *

UNITED STATES PATENT AND TRADEMARK OFFICE
CERTIFICATE OF CORRECTION

PATENT NO. : 9,937,053 B2
APPLICATION NO. : 14/532636
DATED : April 10, 2018
INVENTOR(S) : Melkent et al.

Page 1 of 1

It is certified that error appears in the above-identified patent and that said Letters Patent is hereby corrected as shown below:

In the Specification

In Column 2, Line 66, delete "implant" and insert -- implant in --, therefor.

In Column 3, Line 16, delete "position." and insert -- position; --, therefor.

In Column 5, Line 2, delete "unexpended" and insert -- unexpanded --, therefor.

In Column 5, Line 9, delete "bone graft storage portion 46" and insert -- bone graft storage portion 38 --, therefor.

In the Claims

In Column 7, Line 56, in Claim 12, delete "bone growth storage portion" and insert -- bone graft storage portion --, therefor.

In Column 8, Line 13, in Claim 16, delete "vertical" and insert -- vertical, --, therefor.

In Column 8, Line 27, in Claim 20, delete "end the" and insert -- end, the --, therefor.

Signed and Sealed this
Seventh Day of May, 2019

Andrei Iancu
*Director of the United States Patent and Trademark Office*